United States Patent
Saget et al.

(10) Patent No.: US 10,258,427 B2
(45) Date of Patent: Apr. 16, 2019

(54) MIXED REALITY IMAGING APPARATUS AND SURGICAL SUITE

(71) Applicants: Edouard Saget, Salt Lake City, UT (US); Richard Boddington, Salt Lake City, UT (US)

(72) Inventors: Edouard Saget, Salt Lake City, UT (US); Richard Boddington, Salt Lake City, UT (US)

(73) Assignee: Orthogrid Systems, Inc., Millcreek, UT (US)

( * ) Notice: Subject to any disclaimer, the term of this patent is extended or adjusted under 35 U.S.C. 154(b) by 0 days.

(21) Appl. No.: 16/028,362

(22) Filed: Jul. 5, 2018

(65) Prior Publication Data
US 2018/0338814 A1    Nov. 29, 2018

Related U.S. Application Data

(62) Division of application No. 15/384,034, filed on Dec. 19, 2016, now Pat. No. 10,052,170.
(Continued)

(51) Int. Cl.
| | |
|---|---|
| G06T 19/00 | (2011.01) |
| A61B 90/00 | (2016.01) |
| G06T 11/60 | (2006.01) |
| G02B 27/01 | (2006.01) |
| G06T 5/00 | (2006.01) |
| G02B 27/22 | (2018.01) |

(52) U.S. Cl.
CPC ............ *A61B 90/37* (2016.02); *G02B 27/017* (2013.01); *G02B 27/225* (2013.01); *G06T 5/006* (2013.01); *G06T 11/60* (2013.01); *G06T 19/006* (2013.01); *A61B 2090/365* (2016.02); *A61B 2090/376* (2016.02); *G06T 2200/24* (2013.01); *G06T 2207/10116* (2013.01); *G06T 2207/20221* (2013.01); *G06T 2207/30008* (2013.01); *G06T 2207/30204* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 9,248,000 B2 * | 2/2016 | Sarvestani | A61B 34/20 |
| 9,436,993 B1 * | 9/2016 | Stolka | G06T 5/001 |

(Continued)

*Primary Examiner* — Ryan M Gray
(74) *Attorney, Agent, or Firm* — Veritay Group IP; Susan Fentress

(57) ABSTRACT

System and method for use of mixed and augmented reality Imaging surgical suite and an augmented reality device are provided. A 2D/3D virtual grid having a head-up display with augmented reality is provided. The head-up display can display a 2D radiographic image or 3D volumetric representation or shape model of image, and can further display an augmented reality grid/indicator which can be depicted as a grid, implant, instrument or bone avatar/figure representing shapes, orientations, and positions relative to an anatomical image or model. The augmented reality indicator can be displayed directly in a surgeon's field of view to provide a live, intra-operative situational environment and navigational guidance for the surgeon. The head-up display can show avatar grids/indicators that are outside of the surgeon's field of view within a patient's body.

16 Claims, 5 Drawing Sheets

Related U.S. Application Data

(60) Provisional application No. 62/357,374, filed on Jul. 1, 2016, provisional application No. 62/269,698, filed on Dec. 18, 2015.

(56) References Cited

U.S. PATENT DOCUMENTS

| | | | | |
|---|---|---|---|---|
| 9,538,962 B1* | 1/2017 | Hannaford | | A61B 5/7445 |
| 9,675,319 B1* | 6/2017 | Razzaque | | A61B 8/0841 |
| 2006/0173290 A1* | 8/2006 | Lavallee | | A61B 34/20 |
| | | | | 600/424 |
| 2007/0236514 A1* | 10/2007 | Agusanto | | A61B 1/00193 |
| | | | | 345/646 |
| 2010/0100081 A1* | 4/2010 | Tuma | | A61B 34/20 |
| | | | | 606/1 |
| 2010/0266171 A1* | 10/2010 | Wendler | | G01T 1/161 |
| | | | | 382/128 |
| 2011/0046483 A1* | 2/2011 | Fuchs | | A61B 8/00 |
| | | | | 600/439 |
| 2011/0102549 A1* | 5/2011 | Takahashi | | A61C 1/084 |
| | | | | 348/46 |
| 2013/0060146 A1* | 3/2013 | Yang | | A61B 5/055 |
| | | | | 600/476 |
| 2013/0245461 A1* | 9/2013 | Maier-Hein | | A61B 5/0035 |
| | | | | 600/476 |
| 2014/0142426 A1* | 5/2014 | Razzaque | | A61B 18/1477 |
| | | | | 600/424 |
| 2014/0222462 A1* | 8/2014 | Shakil | | G06Q 50/22 |
| | | | | 705/3 |
| 2014/0243614 A1* | 8/2014 | Rothberg | | A61B 8/13 |
| | | | | 600/301 |
| 2014/0275760 A1* | 9/2014 | Lee | | A61B 1/00045 |
| | | | | 600/102 |
| 2014/0276001 A1* | 9/2014 | Ungi | | A61B 8/0841 |
| | | | | 600/424 |
| 2014/0300632 A1* | 10/2014 | Laor | | G06T 19/006 |
| | | | | 345/633 |
| 2015/0049083 A1* | 2/2015 | Bidne | | G06T 19/006 |
| | | | | 345/420 |
| 2016/0154620 A1* | 6/2016 | Tsuda | | G06F 19/3481 |
| | | | | 345/633 |
| 2016/0225192 A1* | 8/2016 | Jones | | G06F 3/012 |
| 2016/0235402 A1* | 8/2016 | Chowaniec | | G16H 40/63 |
| 2016/0302747 A1* | 10/2016 | Averbuch | | A61B 6/547 |
| 2017/0231714 A1* | 8/2017 | Kosmecki | | A61B 17/24 |
| | | | | 345/419 |
| 2017/0281297 A1* | 10/2017 | Tuma | | A61B 34/20 |

* cited by examiner

MIXED REALITY IMAGING APPARATUS AND SURGICAL SUITE

CROSS-REFERENCE TO RELATED APPLICATIONS

This application is a divisional patent application of U.S. Ser. No. 15/384,034 filed Dec. 19, 2016 and this application claims the benefit of U.S. provisional patent application No. 62,269,698 filed Dec. 18, 2015, and U.S. provisional patent application No. 62,357,374 filed Jun. 30, 2016, under 35 U.S.C. Sec. 119(e) (hereby incorporated by reference in their entirety).

STATEMENT REGARDING FEDERALLY SPONSORED RESEARCH OR DEVELOPMENT

None.

The names of the parties to a joint research agreement. Orthogrid Systems, S.A.R.L., Richard Boddington, and MediLux Capital Holdings, S.A.R.L.

REFERENCE TO A "SEQUENCE LISTING," A TABLE, OR A COMPUTER PROGRAM LISTING APPENDIX SUBMITTED ON A COMPACT DISC AND AN INCORPORATION-BY-REFERENCE OF THE MATERIAL ON THE COMPACT DISC

None.

FIELD OF THE INVENTION

System and method for intraoperative use of a mixed reality imaging surgical suite and a mixed reality surgical device to provide a graphical user interface for a user.

BACKGROUND OF THE INVENTION

Image guided surgery real-time augmented reality navigation system has been shown using open MRI in laparoscopic surgery. Image-guided laparoscopic surgery in an open MRI operating theater Surg Endosc. 2013 June; 27(6): 2178-84 and Cummingham U.S. Pat. No. 9,123,155 due to conventional techniques and tools for performing laparoscopic procedures may limit the vision of the surgeon. Heads-up displays using GOOGLE GLASS (Mountain View, Calif.) for use in diabetic limb surgery. David Armstrong, A Heads-Up Display for Diabetic Limb Salvage Surgery; J Diabetes Sci Technol v.8(5)(2014).

Surgeons have begun to explore the use of methods to view inside the patient during surgery. Surgeons use radiographic and other imaging modalities in an attempt to view the anatomy during surgery. These systems can be designed to focus a surgeon's attention in front of them instead of other areas within the operating room and distract them during surgery. These head-up displays can include the radiographic or other image and shape model or avatar, such that a surgeon can view the patient bone fracture, for example, without looking up at the monitor. A need exists in the industry to provide a broader range of in-puts to the surgeon that do not require the surgeon to look away from the surgical table.

SUMMARY OF INVENTION

A system is provided that allows head-up displays (HUD) with mixed reality (MR) that includes augmented reality (AR) and/or holography to allow for live visualization of gridded avatars in order to allow for accurate positioning and alignment of implants and/or bones. According to one aspect of the present disclosure, a method for displaying a live, intra-operative situational environment of a mixed reality grid/avatar with 2D anatomical image or a 3D shape model or hologram is provided during a surgical procedure. More specifically, a computerized method of enhancing an intraoperative surgical image displayed to a user, is provided. The process steps include: providing a processor, a memory communicably coupled to the processor, a display communicably coupled to the processor and an image source of an anatomical image, communicably coupled to the processor; receiving a surgical image from the image source; detecting at least one target within the surgical image using the processor; generating an indicator associated with the at least one target using the processor; creating an enhanced image by combining the surgical image with the indicator associated with the at least one target using the processor; and displaying the enhanced image on the display as a graphical user interface.

The method can include upon image acquisition, displaying a virtual grid, avatar or combination thereof representing the implants, instruments and bones. In the most basic form the system is made of: a head-up display, at least one processor, and a memory operatively coupled to the processor, the memory storing program instructions that when executed by the processor, causes the processor to perform the processes.

Generally described, the systems and methods provided herein are directed to content provided on a surgeons' head-up display. The content can be an augmented reality grid or holographic grid or avatar and a 2D/3D image or model for a surgically integrated visual guidance system. The augmented reality grid can be placed in front of the surgeon at an optimal viewing location or position removing the need for focusing outside of a predetermined surgical area.

In another embodiment, a computer implemented system to improve intraoperative efficiency in a musculoskeletal applications is provided. The system includes: a computer system made of a microprocessor and a non-transitory computer-readable storage medium coupled to the microprocessor, wherein the non-transitory computer-readable storage medium is encoded with computer-readable instructions; wherein when the computer-readable instructions are executed, the microprocessor performs the respective functions. The computer system includes: a preoperative sub-artificial reality space; an intraoperative sub-artificial reality space; and a device configured to view an augmented reality field of an operative space and the preoperative sub-artificial reality space and the intraoperative sub-artificial reality space. The system, in one exemplary embodiment, includes a resource sub-space.

DETAILED DESCRIPTION OF THE INVENTION

Figure 1:
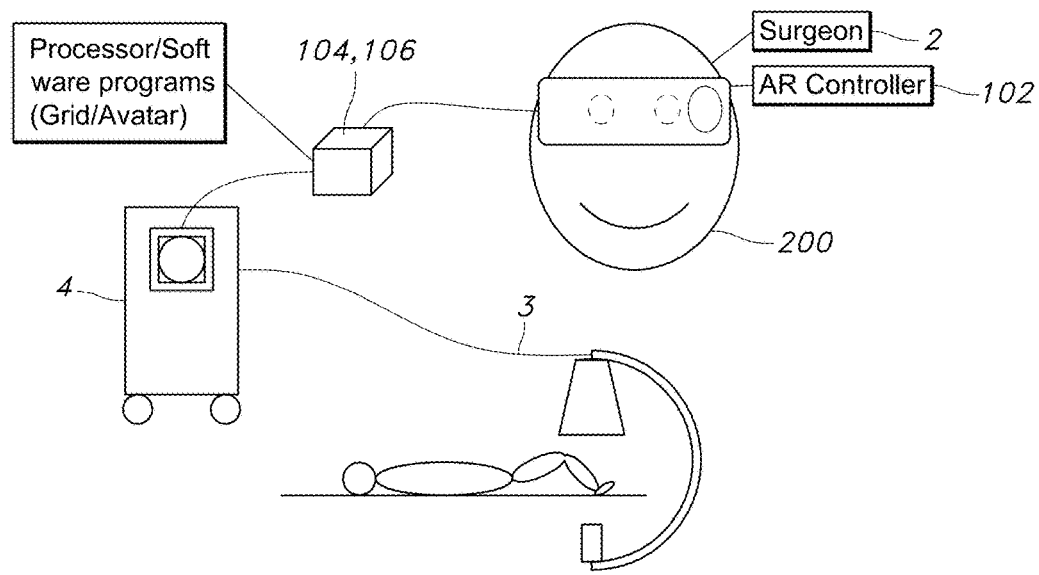
FIG. 1 is a diagram depicting head-up display for showing an augmented reality indicator based visual guidance system.

The present invention may be understood more readily by reference to the following detailed description of the invention. It is to be understood that this invention is not limited to the specific devices, methods, conditions or parameters described herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the inventions, and are not restrictive of the invention as claimed. Unless defined otherwise, all technical and scientific terms used herein have the same meaning as commonly understood by one of ordinary skill in the art to which this invention belongs.

A number of advantages can be provided using the systems and methods described herein. Surgeon distraction can be reduced through the heads-up display as it focuses the surgeons' attention directly in front of them within the field of view. The augmented reality indicator provides a method of visualizing the location of the surgical image and the grids or avatar.

The system includes: virtual reality (VR), which can be referred to as immersive multimedia or computer-simulated reality, that replicates an environment that simulates a physical presence in places in the real world or an imagined world, allowing the user to interact in that world. Virtual reality is the umbrella term for all immersive experiences, which could be created using purely real-world content, purely synthetic content or a hybrid of both. Augmented reality (AR) is a live, direct or indirect view of a physical, real-world environment whose elements are augmented (or supplemented) by computer-generated sensory input such as sound, video, graphics or GPS data.

Augmented reality is an overlay of content on the real world, but that content is not anchored to or part of it. The real-world content and the CG content are not able to respond to each other. Holography is a technique which enables 3D images (holograms) to be made. It involves the use of a laser, interference, diffraction, light intensity recording and suitable illumination of the recording. The image changes as the position and orientation of the viewing system changes in exactly the same way as if the object were still present, thus making it appear 3D.

Mixed reality (MR) sometimes referred to as hybrid reality—is the merging of real and virtual worlds to produce new environments and visualizations where physical and digital objects co-exist and interact in real time. Mixed reality is an overlay of synthetic content on the real world that is anchored to and interacts with the real world—for example, a surgeon overlaying virtual ultrasound images on their patient while performing an operation. The key characteristic of MR is that the synthetic content and the real-world content are able to react to each other in real time. Hardware associated with mixed reality includes HOLOLENS (Microsoft Corporation). An avatar is an "icon" or "figure" or "image" that is used to represent a person or thing in the virtual or augmented reality world of computers.

Now referring to FIG. 1, a typical scenario involves a surgeon 2 having the capability to intra-operatively and in a live, real-time situation, generate and capture an anatomical image (radiographic, ultrasound, etc.) of the patient's relevant procedural surgical site using a intra-operative mobile imaging system 4. A surgical image 3 is transferred to a computer control system including: a processor 104 and software programs 106. The software programs 106 are configured to generate an indicator which in one exemplary embodiment is a grid. A grid is a pattern or template used to define alignment parameters of anatomy and implant placement in a patient. The grid can include any shape or pattern of geometric nature or text to reference angles, length positioning or targeting. The grid can be a single line, a geometrical pattern, number, letter or a complex pattern of multiple lines and geometries that correspond to surgical variables. The grid patterns can be predesigned or constructed intra-operatively in real-time based upon the surgeon's knowledge of anatomy and clinical experience including interpretation of morphometric literature and studies identifying key relationships and dimensions between anatomical landmarks and its application in supporting good surgical technique as it relates to specific procedures. In another embodiment, the indicator is an avatar. An avatar is a representative object such as an implant, an instrument and a bone.

The content directed to the mixed reality controller 102 can include any and all of the following: statistical shape models or atlases derived from clinical data, 2D anatomical image, software generated 3D model of bony architecture, software generated 3D model of implant, 3D model of instrument, trackable shape(s), distortion adaptation algorithm, auto tracking algorithm, segmentation algorithm to work individually or synergistically with an integrated mixed reality grid or avatar representation displayed simultaneously defining relative position, shape, orientation and distance of defined matching targeted coordinates and anatomical points or landmarks. A volumetric head-up display (HUD) 200 is configured to be capable of rendering volumetric contact-analog augmented reality graphic elements (e.g., 3-dimensional or "3-D" graphic elements rendered into the same space as the real environment) with correctly reproduced depth cues. The head-up display projects graphic elements, such as contact-analog augmented reality implant, instrument, or bone models directly to the user along with the grid display. The benefit of this type of direct display is the user does not need to look up to view a separate screen as the surgical images are viewed simultaneously.

Figure 2:
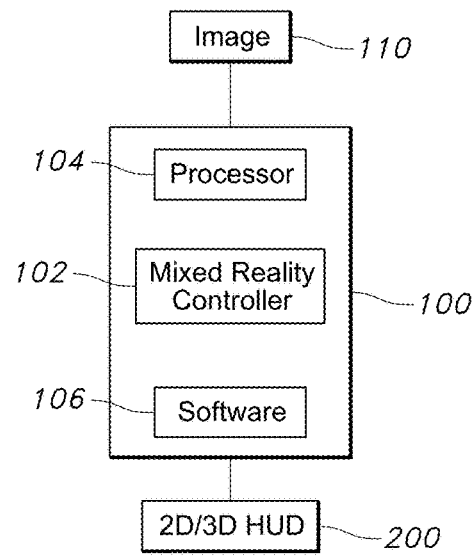
FIG. 2 is a block diagram of the system.

Referring to FIG. 2, a block diagram of an exemplary mixed reality heads up device 100 is provided. The heads-up device 100 is in communication with the volumetric head-up display 200. The heads-up device 100 can include an augmented reality or mixed reality controller 102 which has a processor 104 to execute software 106 instructions to perform operations of: capture, transfer, and display intraoperative image 110. The software 106 is configured to: two dimensionally map an augmented or mixed reality radiographic image on the head-up display, or three dimensionally mapping an augmented reality or mixed reality volumetric shape model of anatomical image on the head-up display: two or three dimensionally map an augmented reality grid/avatar on the head-up display; and spatially overlay and match selected targeted anatomical points of the grid/avatar and image, and then simultaneously projected by the head-up display, auto track, live, intra-operatively the targeted points. In another embodiment, the software 106 is configured to display a distortion adapted/corrected grid/avatar relative to a distortion adapted/corrected image of the anatomical structures.

Figure 3:
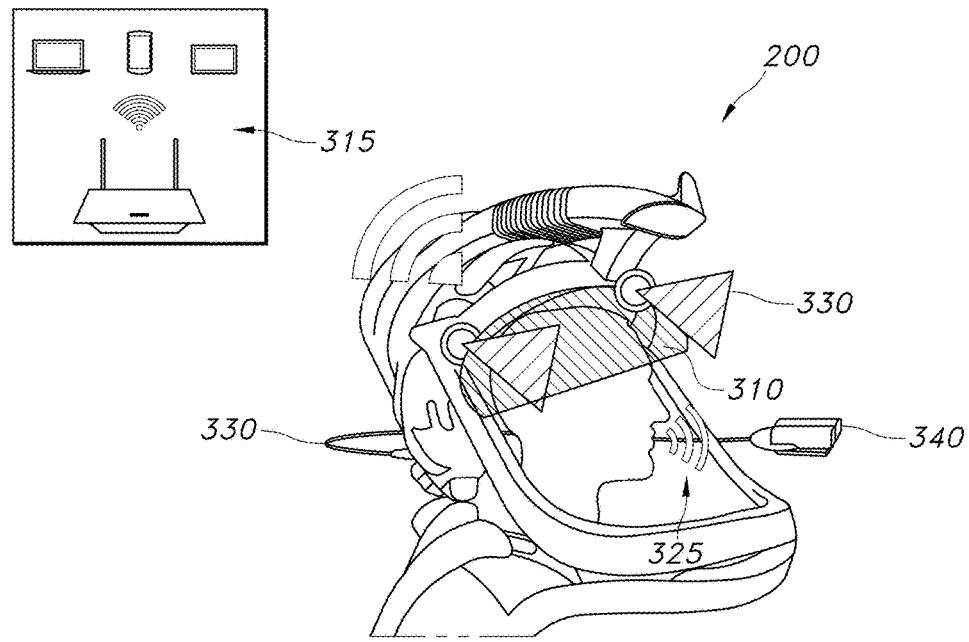
FIG. 3 is an illustrative of a mixed reality controller enabling HUD.

Now referring to FIG. 3, the HUD 200 equipment includes: a mixed reality visualization and controller component that includes: Augmented Reality/Holographic display of grid and anatomy (2D and 3D). Auto real-time, intra-operative selection/recognition/segmentation of anatomical image (X-ray, Fluoro, CT, MRI) and anatomical landmarks (points, lines, geometrical shapes etc) and auto-snap/position/placement of an AR/Holo grid on image or statistical shape modeled image of anatomical bones. The grid defines alignment parameters of anatomy and implant placement. Measurements and data can be displayed on AR/Holo lenses, glasses, or heads-up display. Applications include hip, knee, shoulder, elbow, and ankle arthroplasty, trauma fractures and limb deformity correction and spine, and sports medicine procedures such as FAI. Capability to micro-display off to the side of direct vision—visualize and work with digital display/graphic/grid in relation to the operating room and patient setting.

In an exemplary system, the intra-operative mobile imaging system 4 is fluoroscopic equipment including a radioactive ion beam emitter and a fluorescent detector that captures the radioactive ion beam and forms a digital image. In one embodiment, the radioactive ion beam emitter is an x-ray emitter and is mounted at one end of the C-arm while the fluorescent detector is an x-ray detector and is mounted at the opposite side of the C-arm. Both the radioactive ion beam emitter and a fluorescent detector are coupled to a computer. The computer includes one or more processors and a non-transitory computer-readable storage medium coupled to the processor 104.

In one embodiment, the electronic display screen is an electronic display device 310, such as a computer monitor, or a heads-up display, such as MOVERIO (Epson). In another embodiment, the electronic display screen is a video fpv goggles with computer-readable instructions which form the software 106 system. The HUD 200 equipment typically includes a network connection 315, video/motion control 320, voice control 325, wired connectivity 330, and a battery 340.

Figure 4:
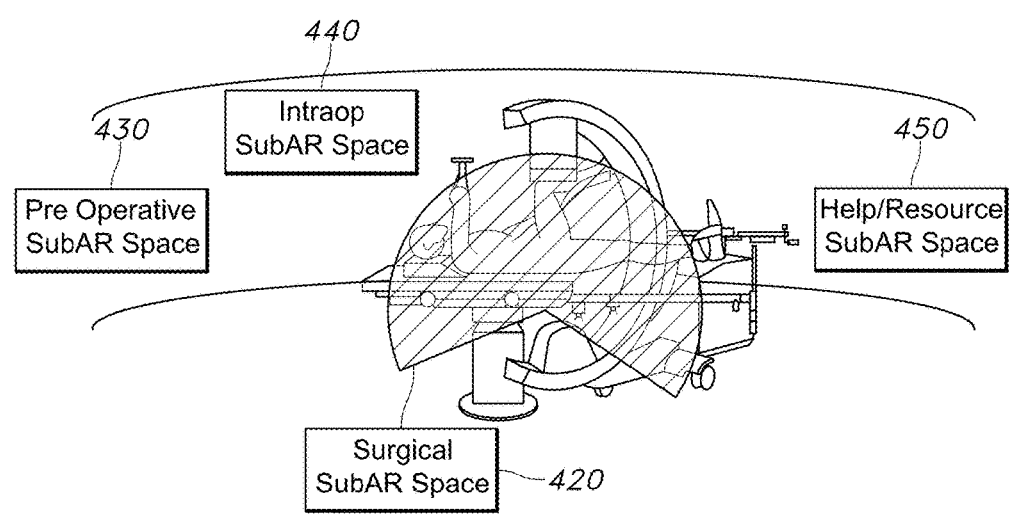
FIG. 4 is a system configuration diagram of the computer-aided surgical operation system of the present invention.
Figure 5A:
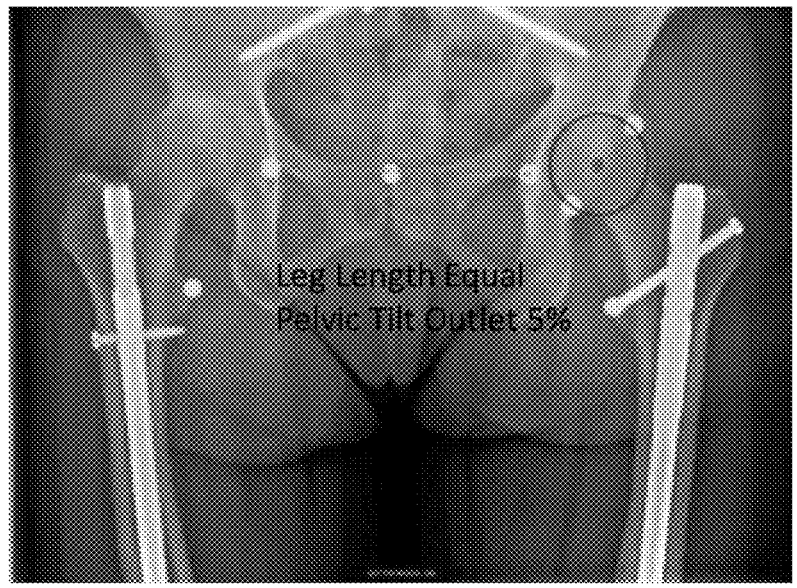
FIG. 5A is an example of a data set related to pre-operative AR sub-space of the present invention.
Figure 5B:
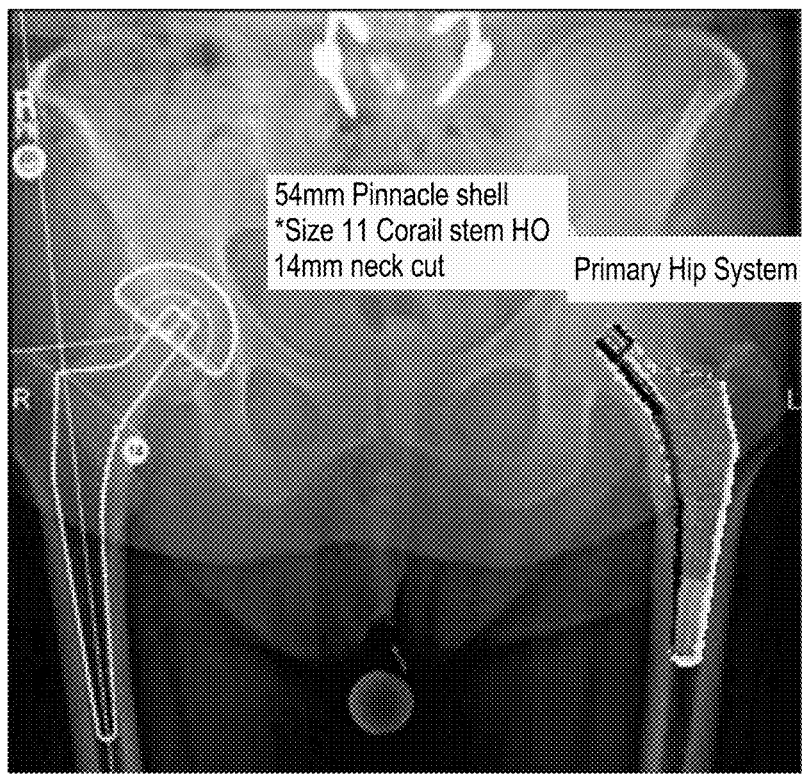
FIG. 5B is an example of a data set related to pre-operative AR sub-space of the present invention.

Now referring to FIG. 4, an augmented reality imaging and surgical suite for the intraoperative efficiency is provided. Augmented reality visualization technology, is used to provide modules (suite of spaces) to a user, such as a surgeon. These suites of spaces include virtual subspaces, each containing individual workspaces and communicating data for display and use before, during and after surgery 2. In use, a device configured to view an augmented reality field of an operative space, such as HUD 200 glasses or as an attachment to a surgical helmet. The surgeon 2 stands in a virtual space that augments the surgical field 420 with a purpose to make available data sets relevant to the performance of the surgery.

For example, an embodiment of the virtual surgical suite includes multiple sub virtual reality spaces. The pre-operative space 430, the Intraoperative space 440 including imaging/templating/Intraoperative space: operating room data set e.g., live feed of medical imaging or other digitally-produced/translated data set of instruments or devices); surgical space: e.g. space left free for clear visualization of the surgical field. Additionally, relevant sub-data sets are called to display within the surgical space temporarily or permanently (user discretion) to facilitate the navigation of instruments/implants or the performance of the surgery; Help Space 450: includes resources such as relevant medical device information/specs such as implant sizes, angles, or education video or patient specific data set such as key medical record etc. Any of these spaces are positioned anywhere at the surgeon preference or in accordance to the best position for each procedure and the side of patient to be operated on.

Figure 6:
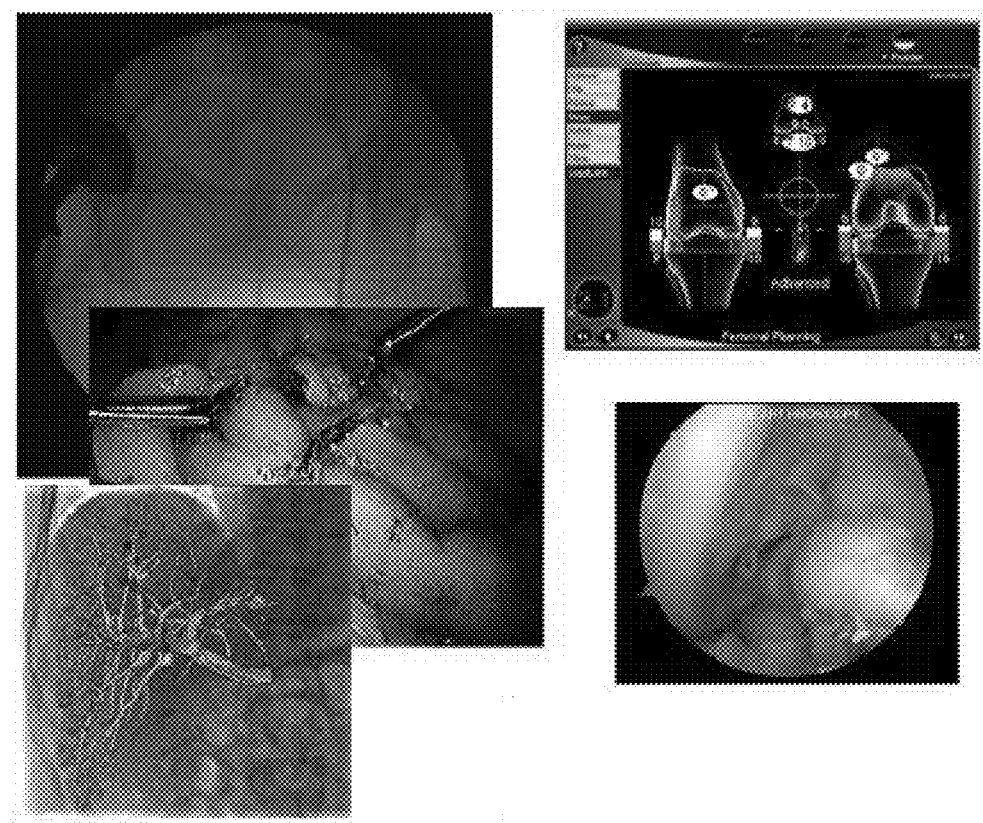
FIG. 6 is an example of a data set related to intra-operative AR sub-space of the present invention.

FIGS. 4-7 show illustrative embodiments of exemplary sub-spaces. FIGS. 5A and 5B are an example of a data set related to pre-operative artificial reality sub-space of the present invention. FIG. 6 is an example of a data set related to intra-operative artificial reality sub-space of the present invention. More specifically, the medical imaging feed includes: 2D and 3D imaging, a video equipment feed, a computer assisted navigational feed, instruments and implants navigational display, instruments and implants specifications (2D and 3D) and surgical software applications manipulation and command.

Figure 7:
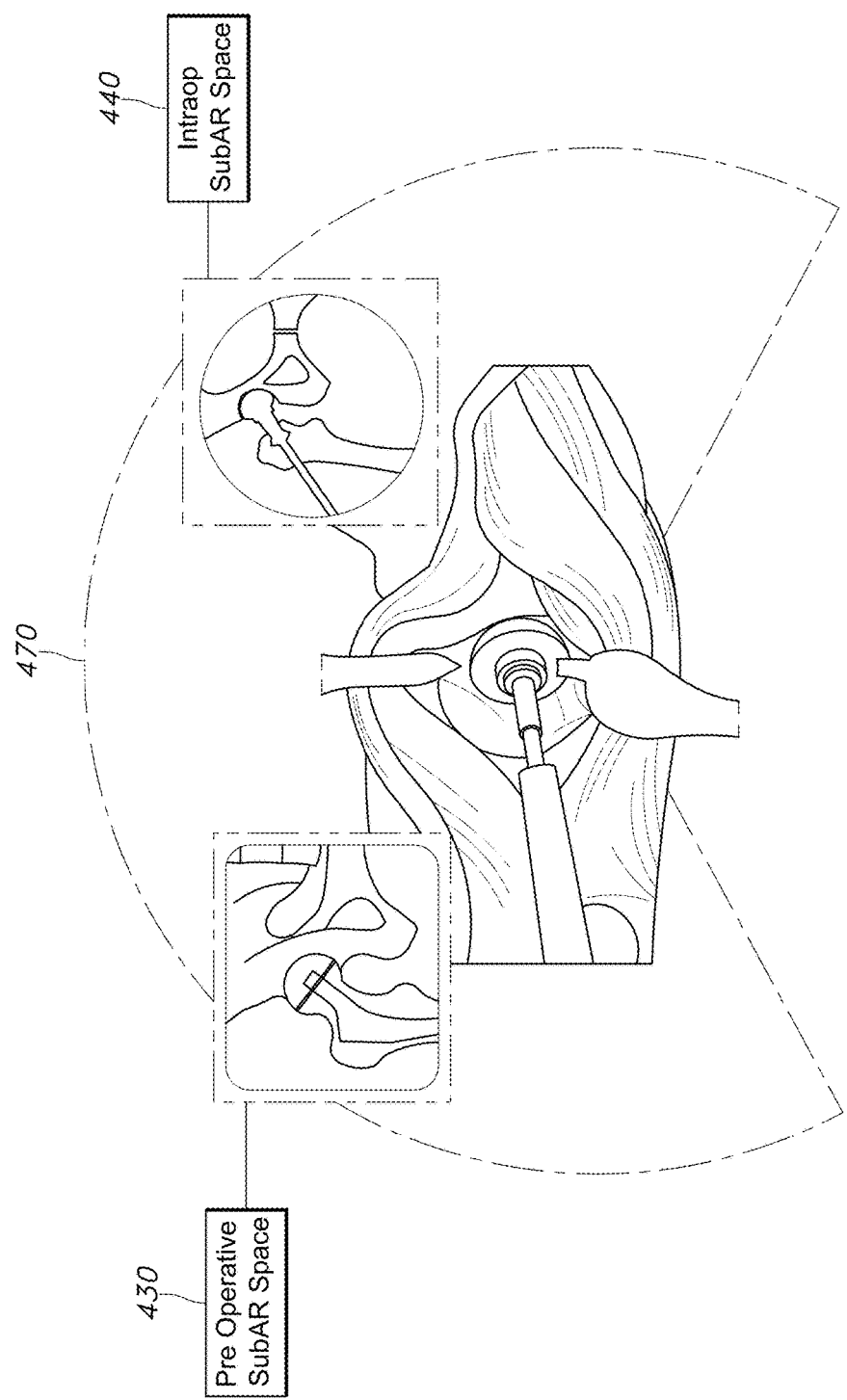
FIG. 7 is an example of a data set related to surgical AR sub-space of the present invention.

Now referring to FIG. 7 is an example of a data set related to surgical artificial reality sub-space 470 of the present invention. The artificial reality sub-space of the present invention is used with anatomical images, such as an X-ray images, of a patient during a surgical procedure. Digital X-ray images are acquired intra-operatively, during surgical procedures, such as joint replacements, and trauma fracture reductions and deformity correction and implant placement/alignment. The acquired image can be viewed or further processed on a display device 200.

The artificial reality sub-space 470 acquired data from the pre-operative SubAR space 430. This data can include temporary or permanent pull of Preoperative or SubAR space data 430. The artificial reality sub-space 470 acquired data from the intra-operative SubAR space 440. This data can include temporary or permanent pull of intra-operative or SubAR space data 440. The artificial reality sub-space 470 includes live overlay of instrument tracking/position/navigation/or artificial reality kit video.

While the invention has been described with reference to preferred and example embodiments, it will be understood by those skilled in the art that a variety of modifications, additions and deletions are within the scope of the invention, as defined by the following claims:

The invention claimed is:

1. A computerized method of enhancing an intraoperative image directly displayed to a user as a graphical user interface, comprising the steps of:

providing a processor, a memory communicably coupled to the processor, a display communicably coupled to the processor and an image source of an anatomical image, communicably coupled to the processor;

receiving the intraoperative image from the image source, wherein the intraoperative image is selected from the group consisting of: an ultrasound, a computed tomography and a magnetic resonance image of a patient during a procedure;

selecting at least one anatomical point within the intraoperative image using the processor;

generating an indicator, wherein said indicator is a grid corresponding to surgical variables associated with the at least one anatomical point using the processor;

creating an enhanced image by combining the intraoperative image with the indicator associated with the at least one anatomical point using the processor; and displaying the enhanced image on the display as a graphical user interface, wherein said image is enhanced with augmented reality data.

2. The method of claim 1 wherein the display is a heads-up display.

3. The method of claim 1 wherein the enhanced image is selected from the group consisting of: an augmented reality image and an augmented reality volumetric shape model of the intraoperative image.

4. The method of claim 1 further comprising the step of adding an avatar as an indicator, wherein the avatar represents an object selected from the group consisting of: an implant, an instrument and a bone.

5. The method of claim 1 wherein creating an enhanced image comprises spatially overlying the at least one anatomical point of the indicator and the intraoperative image.

6. The method of claim 5 further comprising distorting the indicator image.

7. The method of claim 5 further comprising distorting the intraoperative image.

8. An intraoperative surgical system comprising: a non-transitory computer-readable storage medium encoded with computer-readable instructions which form the application software and a processor to process the instructions to:

receive a surgical image from an image source, wherein the surgical image is selected from the group consisting of: an ultrasound, a computed tomography and a magnetic resonance image of a patient during a surgical procedure;

receive a selection of at least one anatomical point within an intraoperative surgical image using the processor;

generate an indicator wherein said indicator is a grid corresponding to surgical variables associated with the at least one anatomical point using the processor;

create an enhanced image by combining the intraoperative surgical image with the indicator associated with the at least one anatomical point using the processor and a device configured to display the enhanced image to a user as a graphical user interface.

9. The intraoperative surgical system of claim 8, wherein the device is a heads-up display comprised of: a mixed reality visualization screen and a controller.

10. The intraoperative surgical system of claim 8, wherein the computer readable storage medium encoded with computer-readable instructions, which form the application software, cause a computer to function as the mixed-reality presentation system.

11. The intraoperative surgical system of claim 9, wherein the enhanced image is selected from the group consisting of: an augmented reality radiographic image and an augmented reality volumetric shape model of the surgical image.

12. The intraoperative surgical system of claim 9 wherein the enhanced image is configured to provide a surgically integrated visual guidance system, wherein said display is selected from the group consisting of: an augmented reality grid, a holographic grid, and an avatar.

13. The intraoperative surgical system of claim 11, wherein the indicator is an avatar.

14. The intraoperative surgical system of claim 8, further comprising
a preoperative sub-artificial reality space; and
an intraoperative sub-artificial reality space and wherein the intraoperative artificial reality sub-space is configured to use an anatomical image.

15. The system of claim 14 further comprising a resource sub-space.

16. The system of claim 8 wherein said surgical procedure is selected from the group consisting of: joint replacements, trauma fracture reductions and deformity correction, implant alignment and implant placement.

* * * * *